US011922722B2

(12) United States Patent
Reddy

(10) Patent No.: US 11,922,722 B2
(45) Date of Patent: Mar. 5, 2024

(54) SYSTEM AND METHOD OF MONITORING ATTRIBUTES ASSOCIATED WITH USERS OF INFORMATION HANDLING SYSTEMS

(71) Applicant: Dell Products L.P., Round Rock, TX (US)

(72) Inventor: Karunakar Palicherla Reddy, Austin, TX (US)

(73) Assignee: Dell Products L.P., Round Rock, TX (US)

( * ) Notice: Subject to any disclaimer, the term of this patent is extended or adjusted under 35 U.S.C. 154(b) by 701 days.

(21) Appl. No.: 17/077,534

(22) Filed: Oct. 22, 2020

(65) Prior Publication Data
US 2022/0129663 A1 Apr. 28, 2022

(51) Int. Cl.
G06V 40/16 (2022.01)
A61B 5/00 (2006.01)
A61B 5/01 (2006.01)
A61B 5/0205 (2006.01)
G06N 3/04 (2023.01)
G16H 40/67 (2018.01)

(52) U.S. Cl.
CPC .......... *G06V 40/165* (2022.01); *A61B 5/0022* (2013.01); *A61B 5/01* (2013.01); *A61B 5/0205* (2013.01); *G06N 3/04* (2013.01); *G16H 40/67* (2018.01)

(58) Field of Classification Search
CPC ....... A61B 5/0022; A61B 5/01; A61B 5/0205; A61B 5/024; A61B 5/0816; A61B 5/6898; A61B 5/746; A61B 2503/20; G16H 40/67; G16H 30/40; G16H 50/30; G06N 3/04; G06N 3/045; G06V 40/165

USPC .......................................................... 382/118
See application file for complete search history.

(56) References Cited

U.S. PATENT DOCUMENTS 10,610,111 B1\* 4/2020 Tran ........................ A61B 5/411
2008/0294012 A1\* 11/2008 Kurtz ...................... A61B 5/444
600/300

(Continued)

OTHER PUBLICATIONS

Ahn, B., Park, J., & Kweon, I. S. (Nov. 2014). Real-time head orientation from a monocular camera using deep neural network. In Asian conference on computer vision (pp. 82-96). Cham: Springer International Publishing. (Year: 2014).\*

(Continued)

*Primary Examiner* — Ross Varndell
*Assistant Examiner* — Emmanuel Silva-Avina
(74) *Attorney, Agent, or Firm* — McDermott Will & Emery LLP

(57) ABSTRACT

In one or more embodiments, one or more systems, one or more methods, and/or one or more processes may determine that a user is in a presence of an information handling system (IHS); determine a digital image of a face of the user; determine an angle of the face of the user with respect to a vertical axis of a camera based at least on the digital image; determine that the face is facing a display associated with the IHS; determine an amount of time, which the user spends looking at the display; determine, via multiple sensors associated with the IHS, a heart rate and a respiratory rate associated with the user; determine that the user should move based at least on the first amount of time, the heart rate, the respiratory rate, and the angle; and display information indicating that the user should move.

19 Claims, 11 Drawing Sheets

(56) References Cited

U.S. PATENT DOCUMENTS

2017/0060254 A1* 3/2017 Molchanov ............ G06N 3/082
2019/0076064 A1* 3/2019 Tahara ................... A61B 5/022
2021/0366606 A1* 11/2021 Shahadi ................. G01S 13/89

OTHER PUBLICATIONS

User Manual for TeraRanger Evo Single Point Distance Sensors and Backboards, TeraRanger Evo by TeraBee, 2018.
CaliPile Infrared Sensing Solutions, TPiS 1S 1385/5029, Excelitas Technologies, www.excolitas.com, Nov. 18, 2016.
24 GHz transceiver—BGT24MTR11: Distance2Go—Xensiv 24 GHz radar demo kit with BGT24MTR11 and XMC4200 32-bit ARM Cortex-M4 MCU for ranging, movement and presence detection. Board version V1.1, Infineon, Sep. 16, 2019.
Cardi/O ATX 2400 Brochure, Retrieved Jul. 7, 2020.
Aging @Home—Touchless Cardiac Monitoring, Cardi/o, Mar. 2020.
Cardi/o Radar Monitor Safety—White Paper, Cardi/o, Mar. 2020.
Remote Cardiac Monitoring, Value-Based Care—White Paper, Jul. 2020.
ROI of Data-Driven Remote Monitoring, Cardi/o, Mar. 2020.
TeraRanger Evo 60m by TeraBee, 2017.
World's smallest Time-of-Flight ranging and gesture detection sensor—VL53L0X Datasheet, STI, Apr. 2018.

* cited by examiner

SYSTEM AND METHOD OF MONITORING ATTRIBUTES ASSOCIATED WITH USERS OF INFORMATION HANDLING SYSTEMS

BACKGROUND

Field of the Disclosure

This disclosure relates generally to information handling systems and more particularly to monitoring attributes associated with users of information handling systems.

Description of the Related Art

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

SUMMARY

In one or more embodiments, one or more systems, one or more methods, and/or one or more processes may determine that a user is in a presence of an information handling system; may determine a digital image of a face of the user; may determine an angle of the face of the user with respect to a vertical axis of the camera based at least on the digital image; may receive the angle of the face of the user with respect to the vertical axis of the camera; may determine, based at least on the angle of the face of the user, that the face of the user is facing a display associated with the information handling system; after determining that the face of the user is facing the display, may determine a first amount of time, which the user spends looking at the display; may determine, via multiple sensors associated with the information handling system, a heart rate associated with the user and a respiratory rate associated with the user; may determine that the user should move based at least on the first amount of time, the heart rate, the respiratory rate, and the angle; and may display, via the display, information indicating that the user should move.

In one or more embodiments, the one or more systems, the one or more methods, and/or the one or more processes may further: determine, based at least on the first amount of time, the heart rate, the respiratory rate, and the angle, that healthcare personnel should be contacted; and in response to determining that the healthcare personnel should be contacted: contact, via a network, the healthcare personnel; and provide, via the network, the heart rate and the respiratory rate to an information handling system associated with the healthcare personnel. In one or more embodiments, the one or more systems, the one or more methods, and/or the one or more processes may further: determine, via a non-contact temperature sensor, a temperature associated with the user; and provide, via the network, the temperature to the information handling system associated with the healthcare personnel.

In one or more embodiments, the one or more systems, the one or more methods, and/or the one or more processes may further: receive, via the network, a teleconference invitation from the information handling system associated with the healthcare personnel; acquire, via the camera, a video stream of the user; and provide, via the network, the video stream of the user to the information handling system associated with the healthcare personnel. In one or more embodiments, the one or more systems, the one or more methods, and/or the one or more processes may further determine a second amount of time, which the user not facing the display. In one or more embodiments, the camera may implement a convolution neural network. For example, to determine the angle of the face of the user with respect to the vertical axis of the camera based at least on the digital image, the convolution neural network may be configured to determine the angle of the face of the user with respect to the vertical axis of the camera based at least on the digital image. In one or more embodiments, the multiple sensors may include a radar device. For example, to determine the heart rate associated with the user and respiratory rate associated with the user, the radar device may be configured to determine at least one of the heart rate associated with the user and respiratory rate associated with the user.

BRIEF DESCRIPTION OF THE DRAWINGS

For a more complete understanding of the present disclosure and its features/advantages, reference is now made to the following description, taken in conjunction with the accompanying drawings, which are not drawn to scale, and in which.

DETAILED DESCRIPTION

Figure 1A:
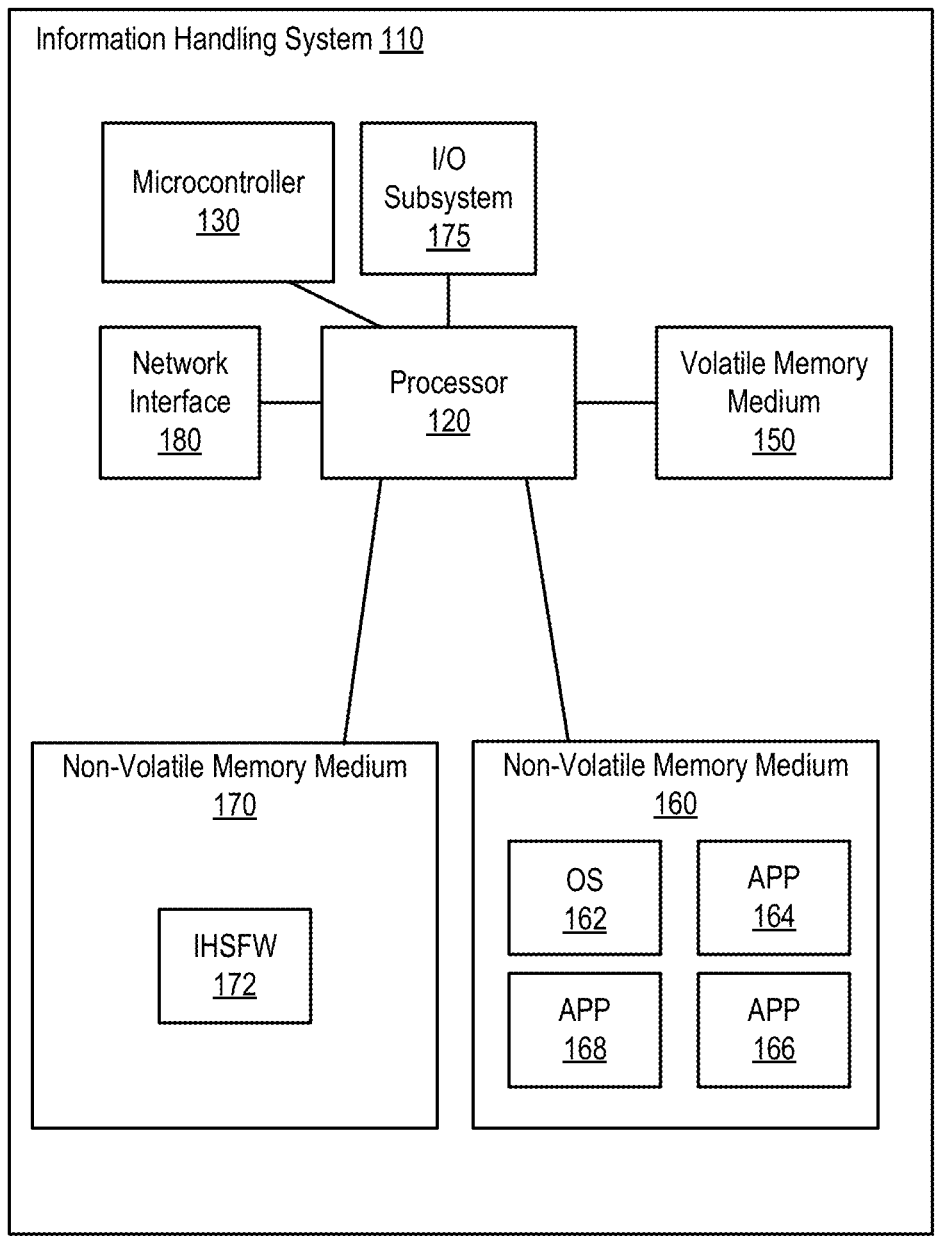
FIG. 1A illustrates an example of an information handling system, according to one or more embodiments.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

In one or more embodiments, a quality of a user's life may be enhanced while preserving a productive atmosphere when the user utilizes an information handling system. For example, the information handling system may determine one or more biometric measurements associated with the user while the user is utilizing the information handling system. In one or more embodiments, an information handling system, such as a smart watch, may provide activity indications and notifications to alert the user, e.g., when movements become restricted, in an attempt to prevent user fatigue. Similar notifications from desktop and/or laptop information handling systems may also provide such notifications to alert the user.

In one or more embodiments, tracking user activity may include an amount of time in front of a display associated with an information handling system (e.g., "screen time"), lack of movement of the user per an amount of time, eyestrain indicators, and/or one or more positions of the user in front of the screen, among others. In one or more embodiments, telemedicine may be utilized to promote health of the user. In one or more embodiments, one or more devices coupled and/or included in the information handling system may determine a heart rate of the user, a respiratory rated of the user, and/or a temperature of the user, among others, may be utilized as at least a portion of a managed healthcare system and/or preventive healthcare system. For example, these biometric measurements may be provided to a healthcare provider. In one instance, these biometric measurements may be utilized to triage users in a telemedicine system. In another instance, these biometric measurements may be utilized by a healthcare provider when a user visits the healthcare provider.

In one or more embodiments, intrusive methods and/or nonintrusive methods may be utilized. A user may opt-in or op-out of one or more intrusive methods and/or one or more nonintrusive methods. In one or more embodiments, one or more systems, one or more methods, and/or one or more processes may utilize low power computer vision with non-intrusive computer vision to determine when a user is in front of a display and/or looking at the display. In one or more embodiments, one or more systems, one or more methods, and/or one or more processes may collect biometric data associated with a user. For example, the user may opt-in to which biometric data associated with the user is collected.

In one or more embodiments, a radar (radio detection and ranging) device and/or a remote temperature determination device may be utilized to collect biometric data associated with the user. For example, one or more devices may collect biometric data with one or more accuracies that are compliant with FDA (Food and Drug Administration) recommended accuracy levels. In one or more embodiments, a radar device may determine one or more of movement of an object, a speed of an object, a velocity of an object (e.g., a speed and an associated direction of the object), a distance to an object, a presence of an object, and an angle of arrival of a signal reflected by an object, among others. In one or more embodiments, a frequency range utilized by a radar device may affect one or more of an antenna size of the radar device, a distance resolution to an object, a jurisdiction-based availability (e.g., available in the United States, available in the European Union, available in Australia, etc.), a wavelength of signals, a signal penetration depth, and a signal attenuation, among others. In one or more embodiments, fatigue and user activity factors, which may not be associated with the FDA, may be collected without utilizing intrusive sensor devices and/or without utilizing high-resolution cameras. For example, a low power vision may provide sufficient biometric data associated with the user to be collected.

In one or more embodiments, one or more systems, one or more methods, and/or one or more processes may utilize a low power vision stream, radar technology that utilizes radio frequencies of an ultra-wideband (e.g., around 60 GHz) and thermopile technology in a small form factor sensor to determine one or more digital wellbeing factors. The one or more digital wellbeing factors may include user activity such as tracking screen time, lack of movements, eyestrain indicators (e.g., blue light exposure), how ergonomically the user is positioned in front of a display, etc. In one or more embodiments, a healthcare professional associated with a telemedicine system may utilize a temperature measurement of the user, a heart rate of the user, and a respiratory rate, among others, to determine a medical course of action. In one example, a medical course of action may include prescribing medication for the user. In another example, a medical course of action may include instructing the user to travel to a physical medical facility, where the user may visit, in person, with a healthcare professional, such as a nurse or a doctor, among others.

In one or more embodiments, one or more systems, one or more methods, and/or one or more processes may alert a user if stress levels increase. A low power computer vision system may collect biometric data, such as a face identification tracking and/or eye tracking. This biometric data may be utilized in telemedicine to guide the user in a remote wellbeing session to position his or her face properly for temperature and other biometric data determinations.

In one or more embodiments, one or more facial identification features in a field of view of a camera may be determined. If a camera is not available for use, a three-dimensional map of facial features of a user may be determined, according to one or more embodiments. For example, the three-dimensional map of facial features of the user may be determined via one or more time-of-flight (ToF) devices. In one or more embodiments, a position of a head of the user may be determined based at least on the three-dimensional map of facial features of the user.

In one or more embodiments, an information handling system may include one or more devices that collect biometric data of a user. In one or more embodiments, one or more devices that collect biometric data of a user may be external to and coupled to an information handling system. For example, one or more devices that collect biometric data of a user may form at least a portion of a modular desktop system. In one or more embodiments, one or more productivity measurements associated with the user may be determined. In one or more embodiments, one or more correlations between biometric data associated with the one or more productivity measurements may be determined. In one or more embodiments, an environment associated with the user may be adjusted based at least on the one or more correlations. For example, the environment associated with the user may be adjusted to maximize a productivity associated with the user.

Turning now to FIG. 1A, an example of an information handling system is illustrated, according to one or more embodiments. An information handling system (IHS) 110 may include a hardware resource or an aggregate of hardware resources operable to compute, classify, process, transmit, receive, retrieve, originate, switch, store, display, manifest, detect, record, reproduce, handle, and/or utilize various forms of information, intelligence, or data for business, scientific, control, entertainment, or other purposes, according to one or more embodiments. For example, IHS 110 may be a personal computer, a desktop computer system, a laptop computer system, a server computer system, a mobile device, a tablet computing device, a personal digital assistant (PDA), a consumer electronic device, an electronic music player, an electronic camera, an electronic video player, a wireless access point, a network storage device, or another suitable device and may vary in size, shape, performance, functionality, and price. In one or more embodiments, a portable IHS 110 may include or have a form factor of that of or similar to one or more of a laptop, a notebook, a telephone, a tablet, and a PDA, among others. For example, a portable IHS 110 may be readily carried and/or transported by a user (e.g., a person). In one or more embodiments, components of IHS 110 may include one or more storage devices, one or more communications ports for communicating with external devices as well as various input and output (I/O) devices, such as a keyboard, a mouse, and a video display, among others. In one or more embodiments, IHS 110 may include one or more buses operable to transmit communication between or among two or more hardware components. In one example, a bus of IHS 110 may include one or more of a memory bus, a peripheral bus, and a local bus, among others. In another example, a bus of IHS 110 may include one or more of a Micro Channel Architecture (MCA) bus, an Industry Standard Architecture (ISA) bus, an Enhanced ISA (EISA) bus, a Peripheral Component Interconnect (PCI) bus, HyperTransport (HT) bus, an inter-integrated circuit ($I^2C$) bus, a serial peripheral interface (SPI) bus, a low pin count (LPC) bus, an enhanced serial peripheral interface (eSPI) bus, a universal serial bus (USB), a system management bus (SMBus), and a Video Electronics Standards Association (VESA) local bus, among others.

In one or more embodiments, IHS 110 may include firmware that controls and/or communicates with one or more hard drives, network circuitry, one or more memory devices, one or more I/O devices, and/or one or more other peripheral devices. For example, firmware may include software embedded in an IHS component utilized to perform tasks. In one or more embodiments, firmware may be stored in non-volatile memory, such as storage that does not lose stored data upon loss of power. In one example, firmware associated with an IHS component may be stored in non-volatile memory that is accessible to one or more IHS components. In another example, firmware associated with an IHS component may be stored in non-volatile memory that may be dedicated to and includes part of that component. For instance, an embedded controller may include firmware that may be stored via non-volatile memory that may be dedicated to and includes part of the embedded controller.

As shown, IHS 110 may include a processor 120, a microcontroller 130, a volatile memory medium 150, non-volatile memory media 160 and 170, an I/O subsystem 175, and a network interface 180. As illustrated, microcontroller 130, volatile memory medium 150, non-volatile memory media 160 and 170, I/O subsystem 175, and network interface 180 may be communicatively coupled to processor 120.

In one or more embodiments, one or more of microcontroller 130, volatile memory medium 150, non-volatile memory media 160 and 170, I/O subsystem 175, and network interface 180 may be communicatively coupled to processor 120 via one or more buses, one or more switches, and/or one or more root complexes, among others. In one example, one or more of volatile memory medium 150, non-volatile memory media 160 and 170, I/O subsystem 175, and network interface 180 may be communicatively coupled to processor 120 via one or more PCI-Express (PCIe) root complexes. In another example, one or more of I/O subsystem 175 and network interface 180 may be communicatively coupled to processor 120 via one or more PCIe switches.

In one or more embodiments, the term "memory medium" may mean a "storage device", a "memory", a "memory device", a "tangible computer readable storage medium", and/or a "computer-readable medium". For example, computer-readable media may include, without limitation, storage media such as a direct access storage device (e.g., a hard disk drive, a floppy disk, etc.), a sequential access storage device (e.g., a tape disk drive), a compact disk (CD), a CD-ROM, a digital versatile disc (DVD), a random access memory (RAM), a read-only memory (ROM), a one-time programmable (OTP) memory, an electrically erasable programmable read-only memory (EEPROM), and/or a flash memory, a solid state drive (SSD), or any combination of the foregoing, among others.

In one or more embodiments, one or more protocols may be utilized in transferring data to and/or from a memory medium. For example, the one or more protocols may include one or more of small computer system interface (SCSI), Serial Attached SCSI (SAS) or another transport that operates with the SCSI protocol, advanced technology attachment (ATA), serial ATA (SATA), a USB interface, an Institute of Electrical and Electronics Engineers (IEEE) 1394 interface, a Thunderbolt interface, an advanced technology attachment packet interface (ATAPI), serial storage architecture (SSA), integrated drive electronics (IDE), or any combination thereof, among others.

Volatile memory medium 150 may include volatile storage such as, for example, RAM, DRAM (dynamic RAM), EDO RAM (extended data out RAM), SRAM (static RAM), etc. One or more of non-volatile memory media 160 and 170 may include nonvolatile storage such as, for example, a read only memory (ROM), a programmable ROM (PROM), an erasable PROM (EPROM), an electrically erasable PROM, NVRAM (non-volatile RAM), ferroelectric RAM (FRAM), a magnetic medium (e.g., a hard drive, a floppy disk, a magnetic tape, etc.), optical storage (e.g., a CD, a DVD, a BLU-RAY disc, etc.), flash memory, a SSD, etc. In one or more embodiments, a memory medium can include one or more volatile storages and/or one or more nonvolatile storages.

In one or more embodiments, network interface 180 may be utilized in communicating with one or more networks and/or one or more other information handling systems. In one example, network interface 180 may enable IHS 110 to communicate via a network utilizing a suitable transmission protocol and/or standard. In a second example, network interface 180 may be coupled to a wired network. In a third example, network interface 180 may be coupled to an optical network. In another example, network interface 180 may be coupled to a wireless network. In one instance, the wireless network may include a cellular telephone network. In a second instance, the wireless network may include a satellite telephone network. In another instance, the wireless network may include a wireless Ethernet network (e.g., a Wi-Fi network, an IEEE 802.11 network, etc.).

In one or more embodiments, network interface 180 may be communicatively coupled via a network to a network storage resource. For example, the network may be implemented as, or may be a part of, a storage area network (SAN), personal area network (PAN), local area network (LAN), a metropolitan area network (MAN), a wide area network (WAN), a wireless local area network (WLAN), a virtual private network (VPN), an intranet, an Internet or another appropriate architecture or system that facilitates the communication of signals, data and/or messages (generally referred to as data). For instance, the network may transmit data utilizing a desired storage and/or communication protocol, including one or more of Fibre Channel, Frame Relay, Asynchronous Transfer Mode (ATM), Internet protocol (IP), other packet-based protocol, Internet SCSI (iSCSI), or any combination thereof, among others.

In one or more embodiments, processor 120 may execute processor instructions in implementing at least a portion of one or more systems, at least a portion of one or more flowcharts, at least a portion of one or more methods, and/or at least a portion of one or more processes described herein. In one example, processor 120 may execute processor instructions from one or more of memory media 150, 160, and 170 in implementing at least a portion of one or more systems, at least a portion of one or more flowcharts, at least a portion of one or more methods, and/or at least a portion of one or more processes described herein. In another example, processor 120 may execute processor instructions via network interface 180 in implementing at least a portion of one or more systems, at least a portion of one or more flowcharts, at least a portion of one or more methods, and/or at least a portion of one or more processes described herein.

In one or more embodiments, processor 120 may include one or more of a system, a device, and an apparatus operable to interpret and/or execute program instructions and/or process data, among others, and may include one or more of a microprocessor, a microcontroller, a digital signal processor (DSP), an application specific integrated circuit (ASIC), and another digital or analog circuitry configured to interpret and/or execute program instructions and/or process data, among others. In one example, processor 120 may interpret and/or execute program instructions and/or process data stored locally (e.g., via memory media 150, 160, and 170 and/or another component of IHS 110). In another example, processor 120 may interpret and/or execute program instructions and/or process data stored remotely (e.g., via a network storage resource).

In one or more embodiments, I/O subsystem 175 may represent a variety of communication interfaces, graphics interfaces, video interfaces, user input interfaces, and/or peripheral interfaces, among others. For example, I/O subsystem 175 may include one or more of a touch panel and a display adapter, among others. For instance, a touch panel may include circuitry that enables touch functionality in conjunction with a display that is driven by a display adapter.

As shown, non-volatile memory medium 160 may include an operating system (OS) 162, and applications (APPs) 164-168. In one or more embodiments, one or more of OS 162 and APPs 164-168 may include processor instructions executable by processor 120. In one example, processor 120 may execute processor instructions of one or more of OS 162 and APPs 164-168 via non-volatile memory medium 160. In another example, one or more portions of the processor instructions of the one or more of OS 162 and APPs 164-168 may be transferred to volatile memory medium 150, and processor 120 may execute the one or more portions of the processor instructions of the one or more of OS 162 and APPs 164-168 via volatile memory medium 150.

As illustrated, non-volatile memory medium 170 may include information handling system firmware (IHSFW) 172. In one or more embodiments, IHSFW 172 may include processor instructions executable by processor 120. For example, IHSFW 172 may include one or more structures and/or one or more functionalities of and/or compliant with one or more of a basic input/output system (BIOS), an Extensible Firmware Interface (EFI), a Unified Extensible Firmware Interface (UEFI), and an Advanced Configuration and Power Interface (ACPI), among others. In one instance, processor 120 may execute processor instructions of IHSFW 172 via non-volatile memory medium 170. In another instance, one or more portions of the processor instructions of IHSFW 172 may be transferred to volatile memory medium 150, and processor 120 may execute the one or more portions of the processor instructions of IHSFW 172 via volatile memory medium 150.

In one or more embodiments, processor 120 and one or more components of IHS 110 may be included in a system-on-chip (SoC). For example, the SoC may include processor 120 and a platform controller hub (not specifically illustrated).

Figure 1B:
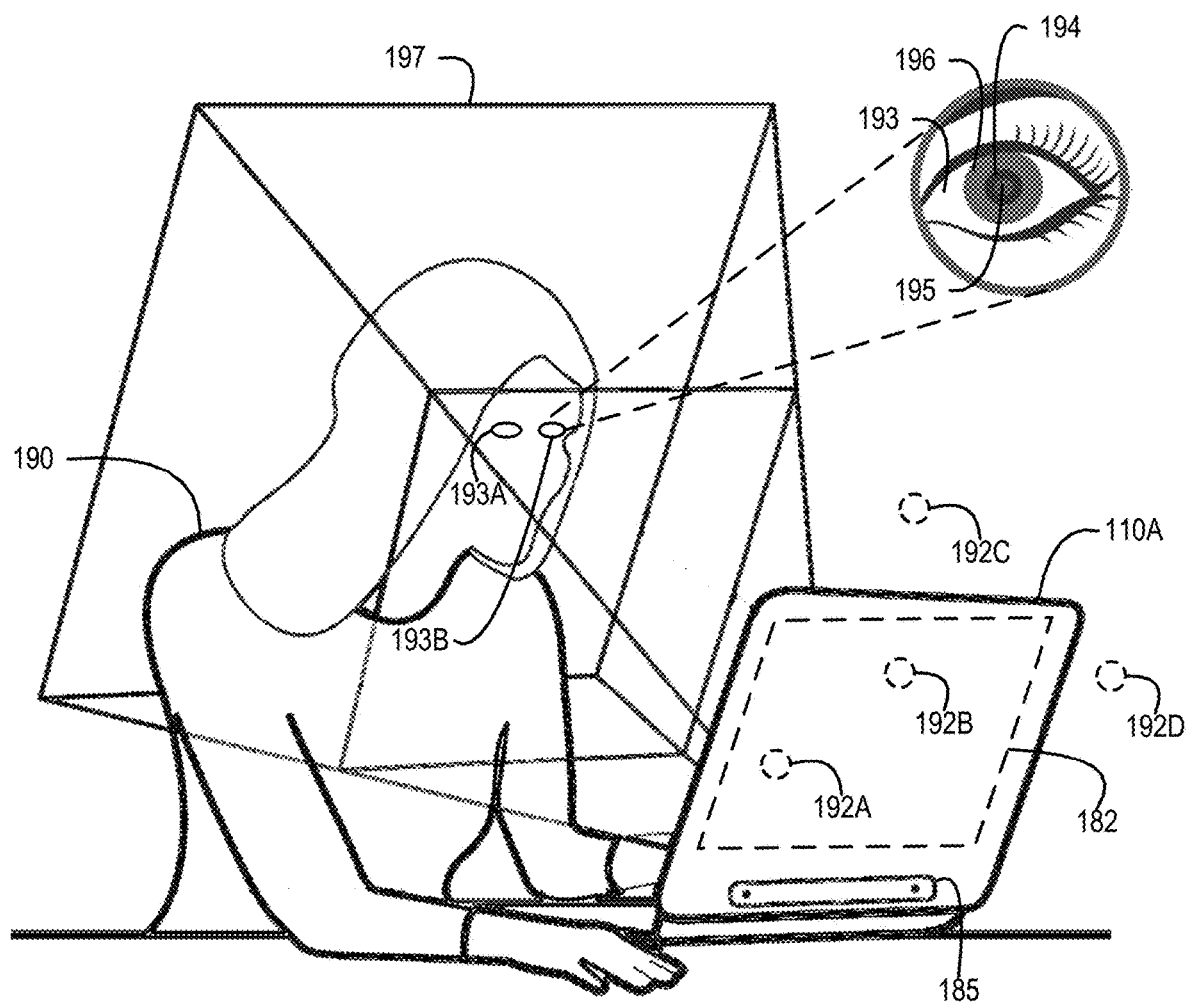
FIG. 1B illustrates an example of a user utilizing an information handling system, according to one or more embodiments.

Turning now to FIG. 1B, an example of a user utilizing an information handling system is illustrated, according to one or more embodiments. As shown, a user 190 (e.g., a person) may utilize an IHS 110A. In one or more embodiments, IHS 110A may include an eye tracking device. For example, the eye tracking device may be communicatively coupled to one or more of processor 120 and microcontroller 130, among others. In one or more embodiments, one or more of camera 184 and eye tracking device 191, among others, may track eyes 193A and 193B of user 190. In one example, one or more of a camera 184 (illustrated in FIG. 1C) and the eye tracking device, among others, may track a pupil 194 of an eye 193. In a second example, one or more of camera 184 and the eye tracking device, among others, may track a center 195 of a pupil 194 of an eye 193. In another example, one or more of camera 184 and the eye tracking device, among others, may track an iris 196 of an eye 193.

In one or more embodiments, one or more of eyes 193A and 193B may be illuminated. For example, IHS 110 may provide light emissions to the one or more of eyes 193A and 193B to illuminate the one or more of eyes 193A and 193B. For instance, the light emissions provided to the one or more of eyes 193A and 193B may be outside a visible spectrum of the one or more of eyes 193A and 193B. As an example, the light emissions provided to the one or more of eyes 193A and 193B may be infrared light emissions. For instance, one or more light emitting diodes (LEDs) may provide the infrared light emissions. In one or more embodiments, IHS 110 may include or be coupled to the one or more LEDs that may provide the infrared light emissions.

In one or more embodiments, one or more of camera 184 and sensors 185, among others, may be utilized in determining a location eyes 193A and 193B are with respect to a field of view 197. In one or more embodiments, a field of view of camera 184 may include field of view 197. In one or more embodiments, one or more of camera 184 and sensors 185, among others, may be utilized in determining gaze points 192A-192D. As shown, gaze points 192A and 192B may be associated with locations of display 182. As illustrated, gaze points 192C and 192D may be associated with locations that are outside display 182. In one or more embodiments, a location of user 190 with respect to field of view 197 may be determined based at least on the location eyes 193A and 193B with respect to field of view 197. In one or more embodiments, a sensor 185 may include one or more of an accelerometer, a magnetometer, a ToF device (e.g., a RADAR device, a LiDAR (light detecting and ranging) device, a SONAR (sound navigation ranging) device, etc.), an eye tracker, a proximity sensor, a temperature sensor, an ambient light sensor, a microphone, a gas sensor (e.g., a volatile organic compound sensor, a $CO_2$ sensor, an $O_2$ sensor, a carbon monoxide sensor, etc.), and an electronic gyroscope, among others.

Figure 1C:
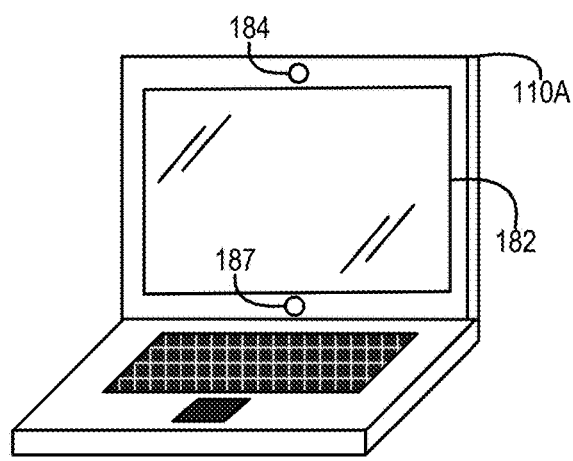
FIG. 1C illustrates a second example of an information handling system, according to one or more embodiments.

Turning now to FIG. 1C, a second example of an information handling system is illustrated, according to one or more embodiments. As shown, IHS 110A may include a camera 184. In one or more embodiments, camera 184 may be communicatively coupled to processor 120. As illustrated, IHS 110A may include a ToF sensor 187. In one or more embodiments, ToF sensor 187 may be communicatively coupled to processor 120.

Figure 1D:
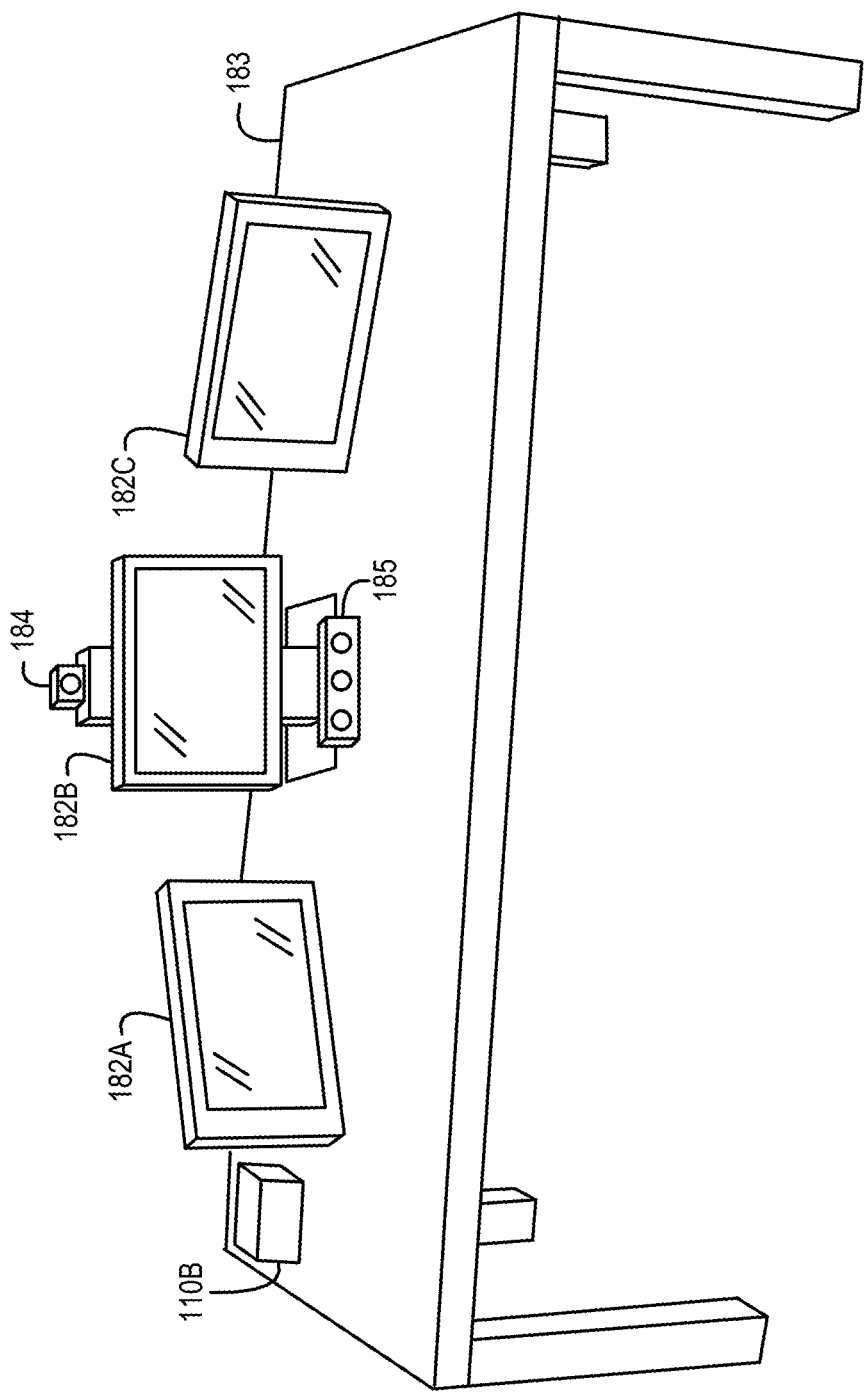
FIG. 1D illustrates another example of an information handling system, according to one or more embodiments.

Turning now to FIG. 1D, another example of an information handling system is illustrated, according to one or more embodiments. As shown, IHS 110B may sit on or may be mounted to a table 183. In one or more embodiments, table 183 may be a desk. In one or more embodiments, IHS 110B may not be configured to be worn by user 190. For example, IHS 110B may not be a wearable device. In one or more embodiments, IHS 110B may coupled communicatively to displays 182A-182C. For example, displays 182A-182C may be external to IHS 110B. In one or more embodiments, IHS 110B may be coupled communicatively to camera 184 and sensors 185. For example, camera 184 and sensors 185 may be external to IHS 110B.

Figure 2:
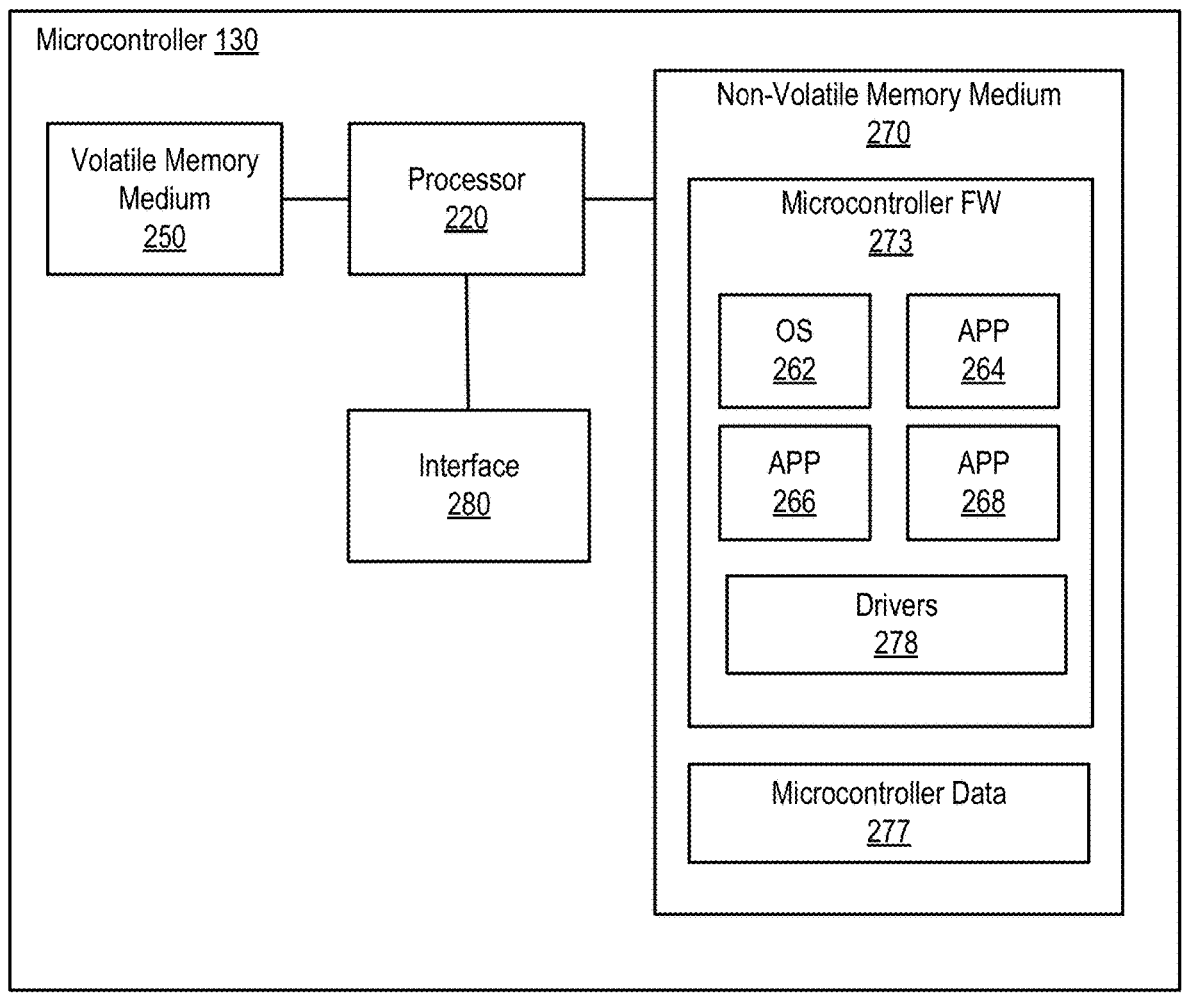
FIG. 2 illustrates an example of a microcontroller, according to one or more embodiments.

Turning now to FIG. 2, an example of a microcontroller is illustrated, according to one or more embodiments. As shown, microcontroller 130 may include a processor 220, a volatile memory medium 250, a non-volatile memory medium 270, and an interface 280. As illustrated, non-volatile memory medium 270 may include microcontroller firmware (FW) 273, which may include an OS 262 and APPs 264-268, and may include microcontroller data 277. For example, OS 262 may be or include a real-time operating system (RTOS). For instance, the RTOS may be or include FreeRTOS, OpenRTOS, SafeRTOS, QNX, ThreadX, VxWorks, NuttX, TI-RTOS, eCos, MicroC/OS, or Zephyr, among others.

In one or more embodiments, microcontroller FW 273 may include drivers 278. For example, driver 278 may include instructions executable by processor 220. In one or more embodiments, the instructions of drivers 278 may be utilized to interface with one or more of sensors 185. For example, one or more of OS 262 and APPs 264-268 may interface with drivers 278, and drivers 278 may interface with the sensors. In one instance, one or more of OS 262 and APPs 264-268 may control one or more of the sensors via drivers 278. In another instance, one or more of OS 262 and APPs 264-268 may receive data from one or more of the sensors via drivers 278.

In one or more embodiments, interface 280 may include circuitry that enables communicatively coupling to one or more devices. In one example, interface 280 may include circuitry that enables communicatively coupling to one or more buses. For instance, the one or more buses may include one or more buses described herein, among others. In a second example, interface 280 may include circuitry that enables one or more interrupt signals to be received. In one instance, interface 280 may include general purpose input/output (GPIO) circuitry, and the GPIO circuitry may enable one or more interrupt signals to be received and/or provided via at least one interrupt line. In another instance, interface 280 may include GPIO circuitry that may enable microcontroller 130 to provide and/or receive signals associated with other circuitry (e.g., diagnostic circuitry, etc.). In a third example, interface 280 may include circuitry that enables communicatively coupling to one or more networks. In one instance, interface 280 may include circuitry that enables communicatively coupling to network interface 180. In another example, interface 280 may include a network interface. In one or more embodiments, interface 280 may be communicatively coupled to one or more of sensors 185.

In one or more embodiments, one or more of OS 262 and APPs 264-268 may include processor instructions executable by processor 220. In one example, processor 220 may execute processor instructions of one or more of OS 262 and APPs 264-268 via non-volatile memory medium 270. In another example, one or more portions of the processor instructions of the one or more of OS 262 and APPs 264-268 may be transferred to volatile memory medium 250, and processor 220 may execute the one or more portions of the processor instructions of the one or more of OS 262 and APPs 264-268 via volatile memory medium 250. In one or more embodiments, processor 220 may execute instructions in accordance with at least a portion of one or more systems, at least a portion of one or more flowcharts, one or more methods, and/or at least a portion of one or more processes described herein. For example, non-volatile memory medium 270 and/or volatile memory medium 250 may store instructions that may be executable in accordance with at least a portion of one or more systems, at least a portion of one or more flowcharts, at least a portion of one or more methods, and/or at least a portion of one or more processes described herein. In one or more embodiments, processor 220 may execute instructions in accordance with at least a portion of one or more of systems, flowcharts, at least a portion of one or more methods, and/or at least a portion of one or more processes described herein. For example, non-volatile memory medium 270 and/or volatile memory medium 250 may store instructions that may be executable in accordance with at least a portion of one or more of systems, at least a portion of one or more flowcharts, at least a portion of one or more methods, and/or at least a portion of one or more processes described herein. In one or more embodiments, processor 220 may utilize microcontroller data 277. In one example, processor 220 may utilize microcontroller data 277 via non-volatile memory medium 270. In another example, one or more portions of microcontroller data 277 may be transferred to volatile memory medium 250, and processor 220 may utilize microcontroller data 277 via volatile memory medium 250.

Figure 3A:
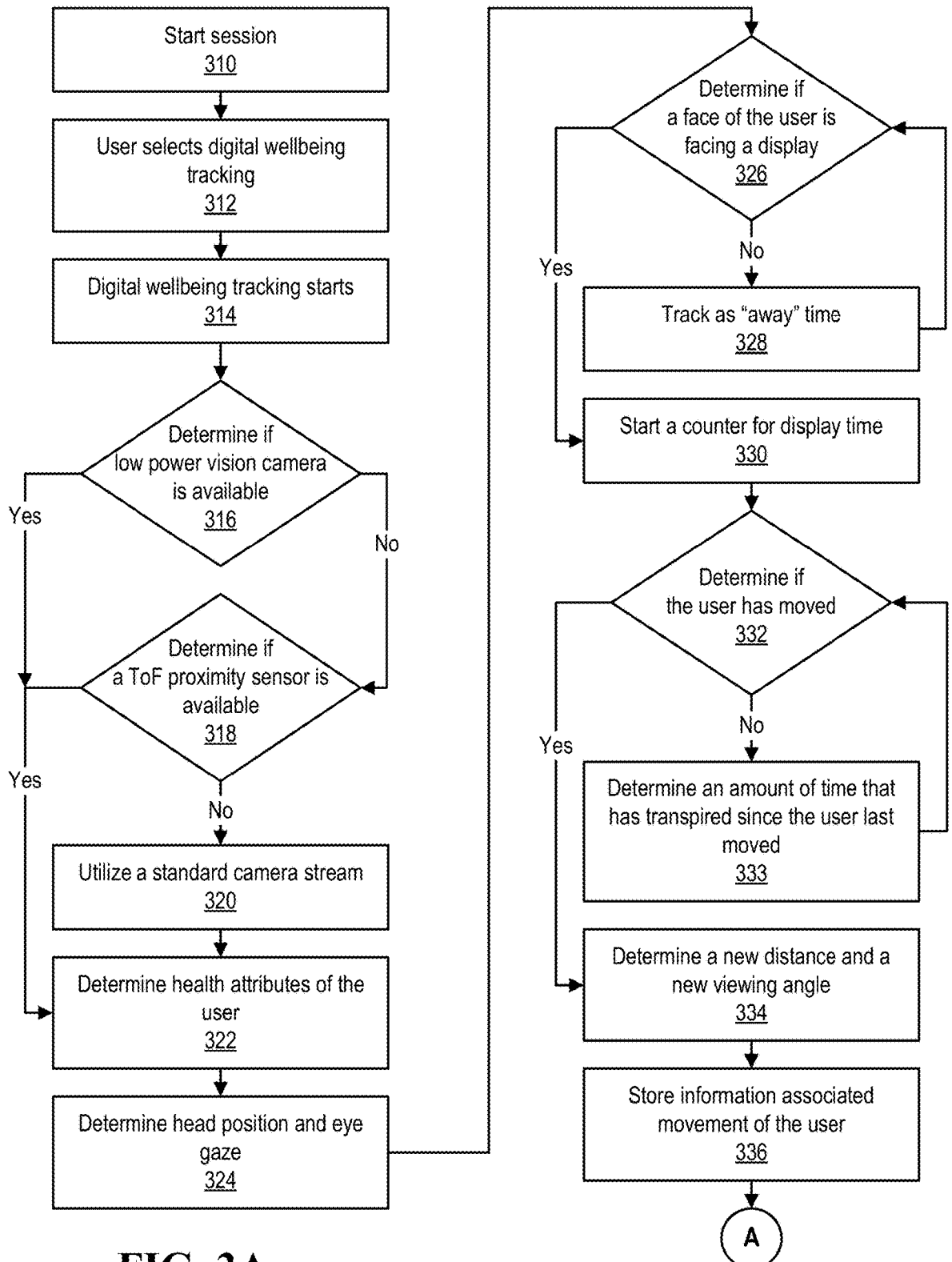
FIGS. 3A and 3B illustrate an example of a method of utilizing a digital wellbeing system, according to one or more embodiments.
Figure 3B:
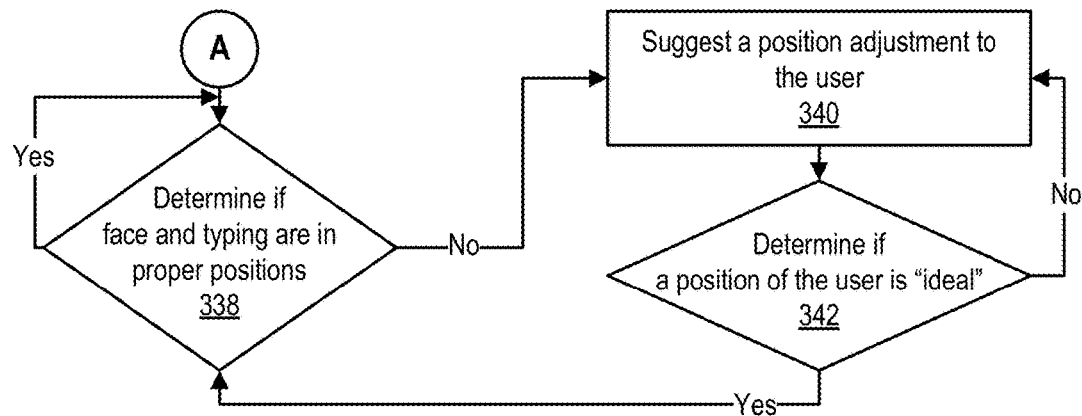

Turning now to FIGS. 3A and 3B, an example of a method of utilizing a digital wellbeing system is illustrated, according to one or more embodiments. At 310, a session may start. At 312, a user may select digital wellbeing tracking. For example, user 190 may opt-in for digital wellbeing tracking via IHS 110. At 314, digital wellbeing tracking may start. At 316, it may be determined if a low power vision camera is available. For example, IHS 110 may be determined if IHS 110 includes a low power vision camera or if IHS 110 is coupled to a low power vision camera. In one or more embodiments, a low power vision camera may include an always on (AON) capability. If a camera includes an AON capability, the camera may include an AON system 538, described with reference to FIG. 5A. If a low power vision camera is not available, it may be determined if a ToF sensor is available, at 318. For example, IHS 110 may be determined if IHS 110 includes a ToF sensor or if IHS 110 is coupled to a ToF sensor.

If a ToF sensor is not available, a standard camera video stream may be utilized, at 320. If a low power vision camera is available or if a ToF sensor is available, health attributes of the user may be determined, at 322. In one example, if a low power vision camera is available, health attributes of the user may be determined via the low power vision camera. In a second example, if a ToF sensor is available, health attributes of the user may be determined via the ToF sensor. In another example, health attributes of the user may be determined via the standard camera stream. In one or more embodiments, the health attributes of the user may include one or more of a heart rate of the user, a respiratory rate of the user, a temperature of the user, a heart rate variability of the user, a respiratory rate variability of the user, an oxygen saturation of the user, and a blood pressure of the user, among others.

At 324, a head position of the user and an eye gaze of the user may be determined. In one example, a head position of user 190 may be determined. In another example, a gaze of eyes 193A and 193B may be determined. For instance, a gaze point 192 (illustrated in FIG. 1B) may be determined. At 326, it may be determined if a face of the user is facing a display. For example, it may be determined if a face of user 190 is facing a display 182. In one or more embodiments, determining if a face of user 190 is facing a display 182 may include determining a gaze point 192. For example, determining if a face of user 190 is facing a display 182 may include determining if a gaze point 192 is associated with a display 182. In one instance, gaze points 192A and 192B may be associated with display 182 (illustrated in FIG. 1B). In another instance, gaze points 192C and 192D may not be associated with display 182 (illustrated in FIG. 1B).

If the face of the user is not facing a display, an "away" time may be tracked, at 328. For example, a counter associated with an amount of time that a user is not facing a display 182 may be started. In one or more embodiments, the method may proceed to 326. If the face of the user is facing a display, a counter associated with an amount of time that a user is facing a display 182 may be started, at 330.

At 332, it may be determined if the user has moved. If the user has not moved, an amount of time that has transpired since the user last moved may be determined, at 333. For example, determining an amount of time that has transpired since the user last moved may be based at least on the counter associated with the amount of time that the user is facing display 182. In one or more embodiments, the method may proceed to 332. If the user has moved, a new distance and a new viewing angle may be determined, at 334. In one example, a new distance and a new viewing angle may be determined via camera 184. In another example, a new distance and a new viewing angle may be determined via one or more of sensors 185. In one instance, a new distance may be determined via one or more of a ToF sensor and a radar sensor, among others. In another instance, a new viewing angle may be determined via one or more of a radar sensor and an eye tracker, among others.

At 336, information associated with movement of the user may be stored. For example, the information associated with movement of user 190 may include one or more of the new distance (e.g., a new distance of user 190 to camera 184, a new distance of user 190 to one or more of sensors 185, etc.), the new viewing angle (e.g., a new viewing angle of a face of user 190 to a display 182, a new viewing angle of eyes 193 of user 190 to a display 182, etc.), a position of a head of user 190, and an amount of time between movements of user 190, among others.

At 338, it may be determined if face and typing are in proper positions. For example, embodiments, determining if face and typing are in proper positions may include determining if user 190 is in a proper ergonomic position. In one instance, determining if user 190 is in a proper ergonomic position may include determining if a spine of user 190 is in a proper alignment. In another instance, determining if user 190 is in a proper ergonomic position may include determining if arms and/or wrists are in positions to avoid or mitigate repetitive stress injuries.

If face and typing are in proper positions, the method may proceed to 338, according to one or more embodiments. If face and typing are not in proper positions, a position adjustment may be suggested to the user, at 340. In one example, a position adjustment suggested to user 190 may include adjusting a distance of user 190 to a display 182. In one instance, a position adjustment suggested to user 190 may include adjusting a distance of user 190 towards display 182. In another instance, a position adjustment suggested to user 190 may include adjusting a distance of user 190 away from display 182. In a second example, a position adjustment suggested to user 190 may include adjusting a height of a display 182. In a third example, a position adjustment suggested to user 190 may include instructing user 190 to get up and/or move around for an amount of time. In another example, a position adjustment suggested to user 190 may include instructing user 190 to move and/or "shake out" hands of user 190 for an amount of time.

At 342, it may be determined if a position of the user is "ideal". For example, determining if a position of the user is "ideal" may include determining if face and typing are in proper positions. For instance, determining if face and typing are in proper positions may be based at least on one or more of a distance (e.g., a distance of user 190 to camera 184, a distance of user 190 to one or more of sensors 185, etc.), a viewing angle (e.g., a viewing angle of a face of user 190 to a display 182, a viewing angle of eyes 193 of user 190 to a display 182, etc.), and a position of a head of user 190, among others. If a position of the user is "ideal", the method may proceed to 338, according to one or more embodiments. If a position of the user is not "ideal", the method may proceed to 340, according to one or more embodiments.

Figure 4A:
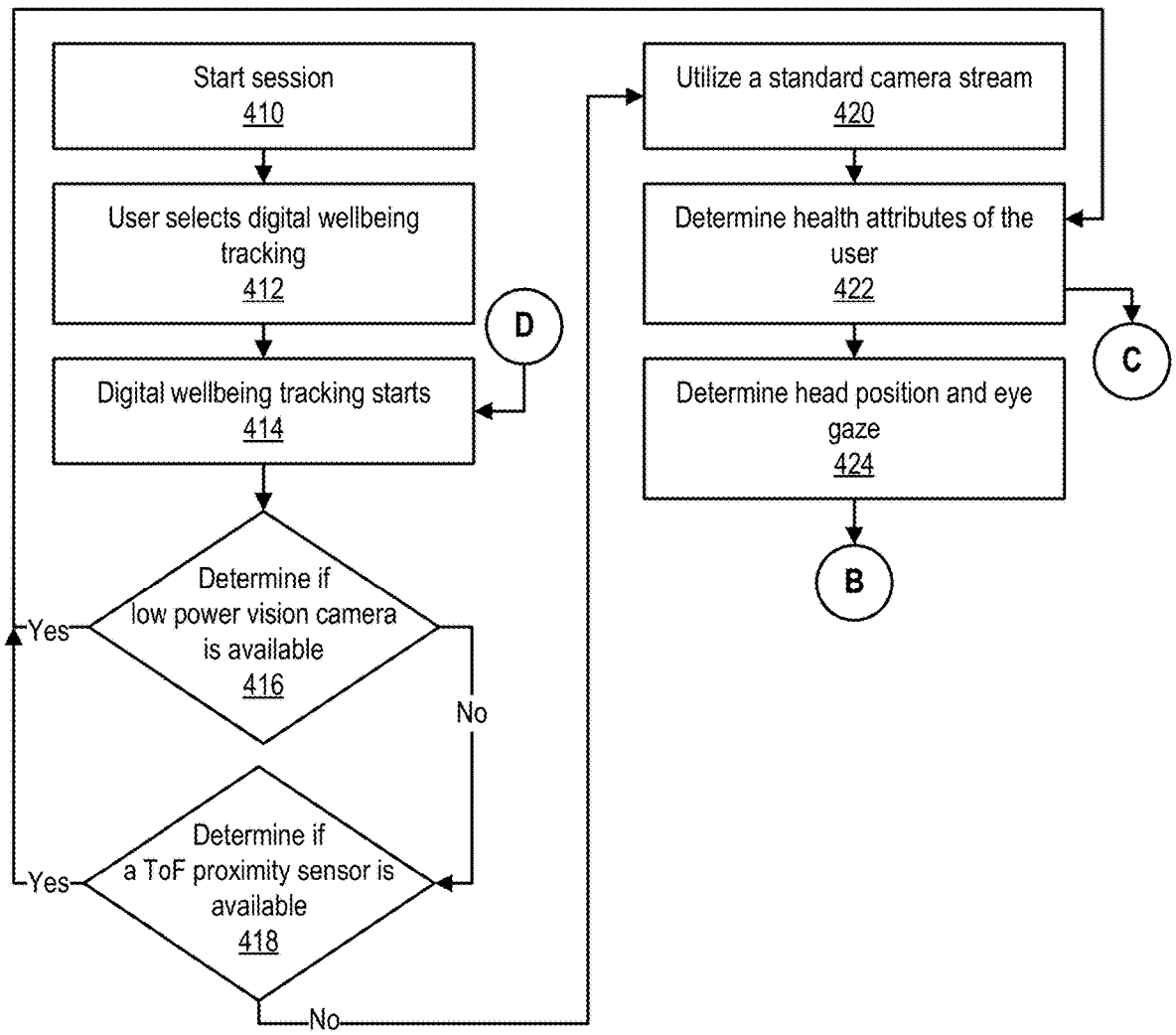
FIGS. 4A and 4B illustrate a second example of a method of utilizing a digital wellbeing system, according to one or more embodiments.
Figure 4B:
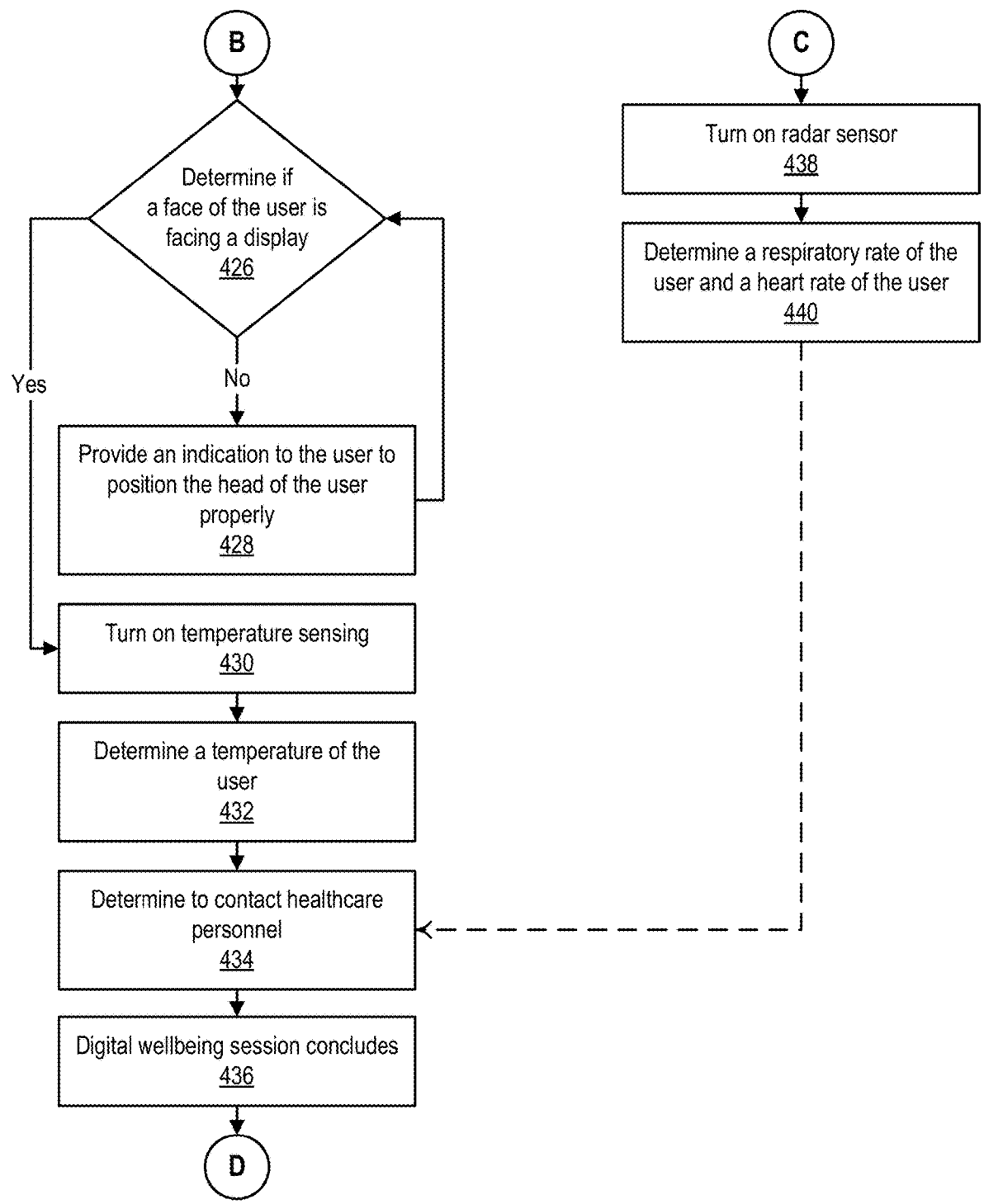

Turning now to FIGS. 4A and 4B, a second example of a method of utilizing a digital wellbeing system is illustrated, according to one or more embodiments. In one or more embodiments, method elements 410-426 may be performed in accordance with method elements 310-326, respectively. If the face of the user is not facing a display, an indication to position the head of the user properly may be provided to the user, at 428. For example, a pop-up window that includes text indicating, to the user, to position the user's head properly may be provided to the user. In one or more embodiments, the method may proceed to 426. If the face of the user is facing a display, temperature sensing may be turned on, at 430. For example, a temperature sensor of sensors 185 may be turned on.

At 432, a temperature of the user may be determined. For example, a temperature of a forehead of the user and/or a temperature of a cheek of the user may be utilized in determining a temperature of the user. In one or more embodiments, a temperature sensor may be utilized in determining a temperature of the user. For example, a temperature sensor may include a thermopile, which may be utilized in determining a temperature of the user. For instance, sensors 185 may include the temperature sensor, which may include a thermopile.

In one or more embodiments, a temperature sensor may include one or more pyrometers, which may receive thermal radiation emitted by a radiating body whose temperature is to be measured at a distance. Thermal radiation may be converted into one or more electrical signals. For example, a temperature of the radiating body may be determined based at least on the one or more electrical signals. In one or more embodiments, a temperature sensor may include a thermocouple. For example, one or more operations of the thermocouple may be based at least on a Seeback effect. For instance, the Seeback effect states that when heat is applied to a first junction (e.g., a hot junction) of dissimilar metals, an electromotive force (e.g., a voltage) may be generated at a second junction (e.g., a cold junction). In one or more embodiments, the electromotive force may be proportional to a difference in temperature between the first junction and the second junction.

At 434, it may be determined to contact healthcare personnel. In one or more embodiments, determining to contact healthcare personnel may be based at least on one or more of the temperature of the user, the heart rate of the user, and the respiratory rate of the user, among others. At 436, the digital wellbeing session may conclude. After the digital wellbeing session concludes the method may proceed to 414, according to one or more embodiments. In one or more embodiments, performing method element 422 may include performing method elements 438 and 440.

At 438, a radar sensor may be turned on. In one or more embodiments, sensors 185 may include the radar sensor. In one or more embodiments, the radar sensor may utilize one or more ultra-wideband (UWB) frequencies. In one or more embodiments, the radar sensor may utilize one or more frequencies of 24 GHz and above. In one or more embodiments, the radar sensor may utilize one or more frequencies between 24 GHz and 60 GHz.

At 440, a heart rate of the user and a respiratory rate of the user may be determined. In one or more embodiments, the radar sensor may be utilized in determining one or more of a heart rate of user 190 and a respiratory rate of user 190, among others. For example, determining to contact healthcare personnel may be based at least on the heart rate of user 190 and the respiratory rate of user 190, among others.

Figure 5A:
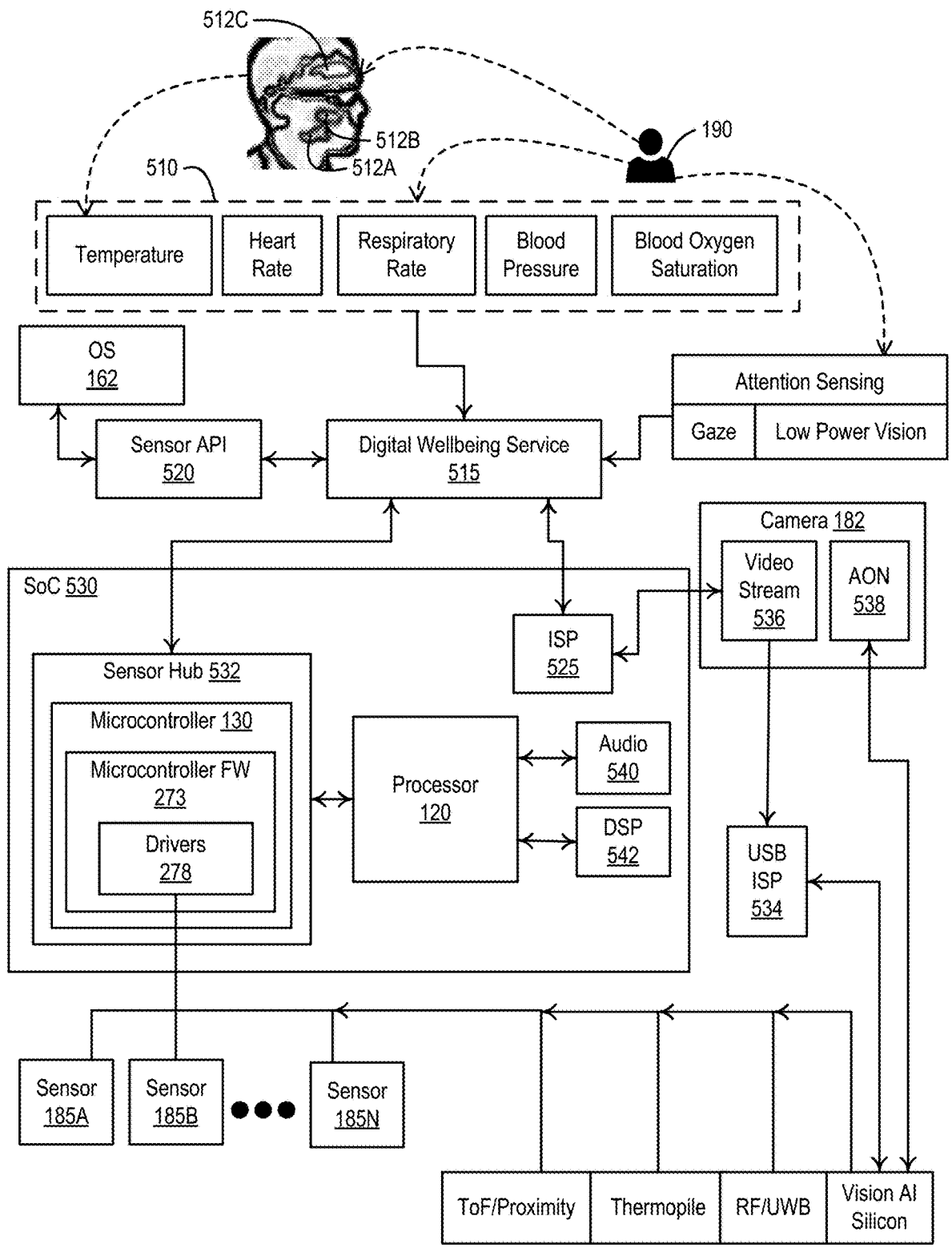
FIG. 5A illustrates an example of a digital wellbeing system, according to one or more embodiments.

Turning now to FIG. 5A, an example of a digital wellbeing system is illustrated, according to one or more embodiments. In one or more embodiments, digital wellbeing system may include an information handling system, a display, a camera, and/or one or more sensors coupled to a microcontroller of the information handling system, among others. As shown, health attributes 510 may be determined from user 190. In one or more embodiments, health attributes 510 may include one or more of a temperature associated with user 190, a heart rate associated with user 190, a respiratory rate associated with user 190, a blood pressure associated with user 190, and a blood oxygen saturation associated with user 190. As illustrated, one or more of heat map areas 512A-512C may be determined. For example, one or more temperatures may be associated with the one or more of heat map areas 512A-512C.

As shown, attention sensing may be determined from user 190. In one example, attention sensing may determine a gaze associated with user 190. For instance, attention sensing may determine one or more of gaze points 192A-192D. In another example, attention sensing may utilize low power vision to determine a presence of user 190 and/or a position of a head of user 190, among others.

In one or more embodiments, a digital wellbeing service 515 may receive health attributes 510. For example, digital wellbeing service 515 may include instructions executable by processor 120. In one or more embodiments, digital wellbeing service 515 may receive attention sensing information. In one or more embodiments, digital wellbeing service 515 may interface with a sensor API 520. For example, sensor API 520 may be an API of OS 162. In one instance, sensor API 520 may be utilized by OS 162 to communicate information to and/or from digital wellbeing service 515. In another instance, sensor API 520 may be utilized by one or more of applications 164-168.

In one or more embodiments, digital wellbeing service 515 may interface with image signal processing (ISP) 525. For example, ISP 525 may communicate information to and/or from a video stream 536 of camera 182. In one or more embodiments, digital wellbeing service 515 may interface with a sensor hub 532. As illustrated, sensor hub 532 may include microcontroller 130. In one or more embodiments, drivers 278 may interface with sensors 185A-185N. For example, one or more of sensors 185A-185N may include a ToF/proximity sensor, a thermopile, a RF/UWB radar, and/or vision artificial intelligence (AI) silicon, among others. Although sensors 185A-185N are illustrated, any number of sensors 185 may be utilized, according to one or more embodiments.

In one or more embodiments, vision AI silicon may communicate information to and/or from a USB ISP 534 and/or an always on (AON) 538 system of camera 182. In one or more embodiments, AON 538 system may determine information based at least on image sensors of camera 182. In one example, AON 538 system may determine an outline of user 190. For instance, the outline of user 192 may be provided via a low-bandwidth bus (e.g., an $I^2C$ bus, a SPI bus, etc.). In another example, AON 538 system may determine a position of a head of user 190 based at least on information from image sensors of camera 182. In one or more embodiments, AON 538 system may include and/or implement a convolution neural network. For example, the convolution neural network may reduce the information from image sensors of camera 182 and determine one or more attributes associated with the head of user 190. In one instance, the convolution neural network may determine an angle of azimuth associated with the head of user 190. In a second instance, the convolution neural network may determine an angle with respect to a horizontal axis. In another instance, the convolution neural network may determine an angle with respect to a vertical axis. As shown, a SoC 530 may include sensor hub 532, processor 120, ISP 525, an audio system 540, and a DSP system 542. In one or more embodiments, IHS 110 may include SoC 530.

Figure 5B:
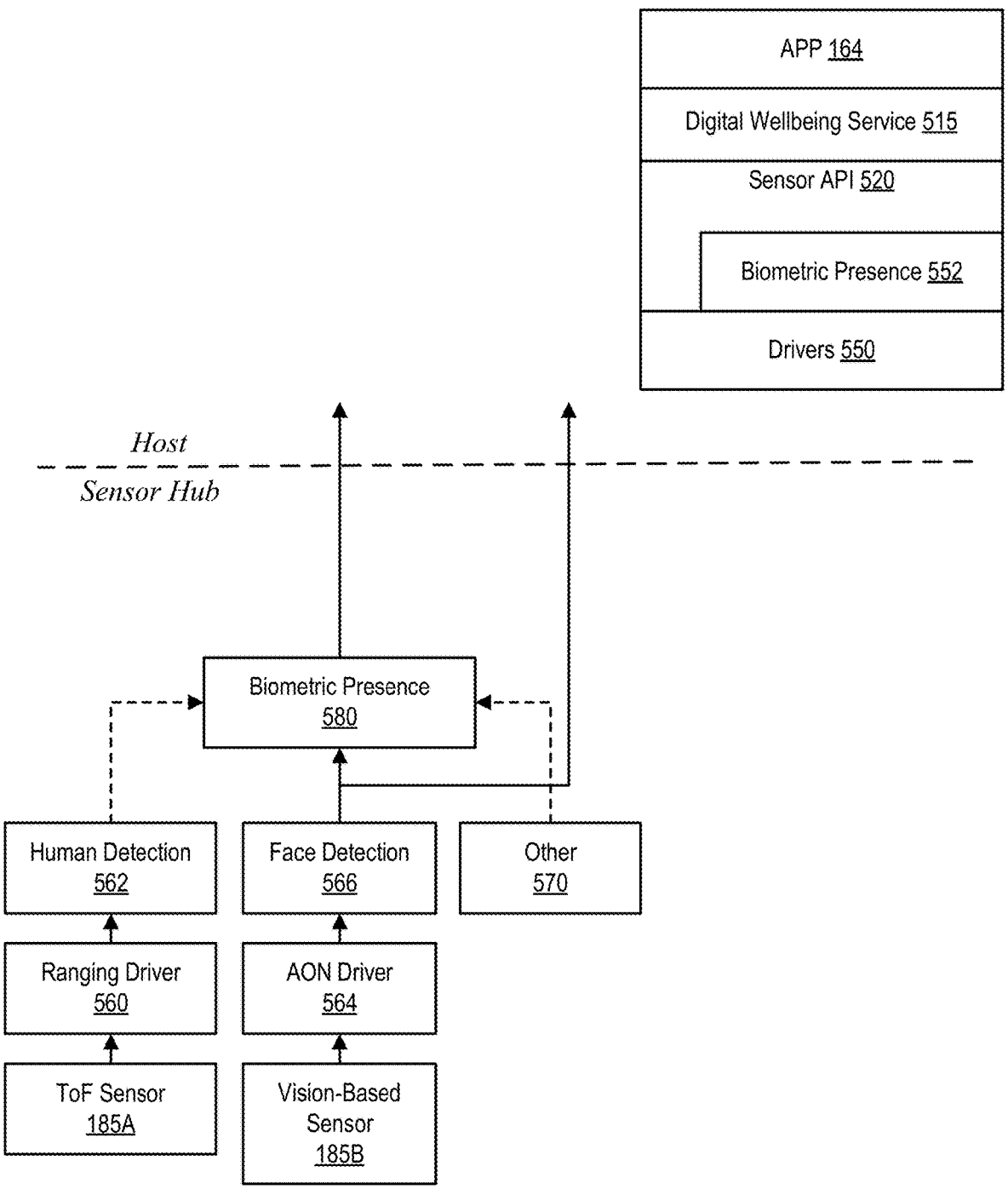
FIG. 5B illustrates an example of a digital wellbeing stack, according to one or more embodiments.

Turning now to FIG. 5B, an example of a digital wellbeing stack is illustrated, according to one or more embodiments. In one or more embodiments, a ToF sensor 185A may provide information to a ranging driver 560. For example, ranging driver 560 may include instructions executable by processor 220 to interface with ToF sensor 185A. In one or more embodiments, ranging driver 560 may provide information to a human detection process 562. For example, human detection process 562 may include instructions executable by processor 220 to determine if a user 190 is present. Human detection process 562 may provide information, indicating whether or not user 190 is present, to a biometric presence process 580.

In one or more embodiments, a vision-based sensor 185B may provide information to an AON driver 564. For example, AON driver 564 may include instructions executable by processor 220 to interface with vision-based sensor 185B. In one or more embodiments, AON driver 564 may provide information to a face detection process 566. For example, face detection process 566 may determine one or more attributes associated with a face of user 190. Face detection process 566 may provide information associated with the attributes associated with the face of user 190 to biometric presence process 580. In one or more embodiments, another process 570 may provide information to biometric presence process 580. For example, other process 570 may provide other biometric information associated with user 190 to biometric presence process 580.

In one or more embodiments, drivers 560 may interface with sensor hub 532. For example, drivers 560 may include one or more device drivers of OS 162. In one or more embodiments, drivers 560 may interface with sensor API 520. Sensor API 520 may include a biometric presence portion 552. For example, biometric presence portion 552 may include a portion of API 520 to interface with biometric presence process 580. In one or more embodiments, sensor API 520 may interface with digital wellbeing service 515. In one or more embodiments, digital wellbeing service 515 may interface with APP 164.

Figure 6A:
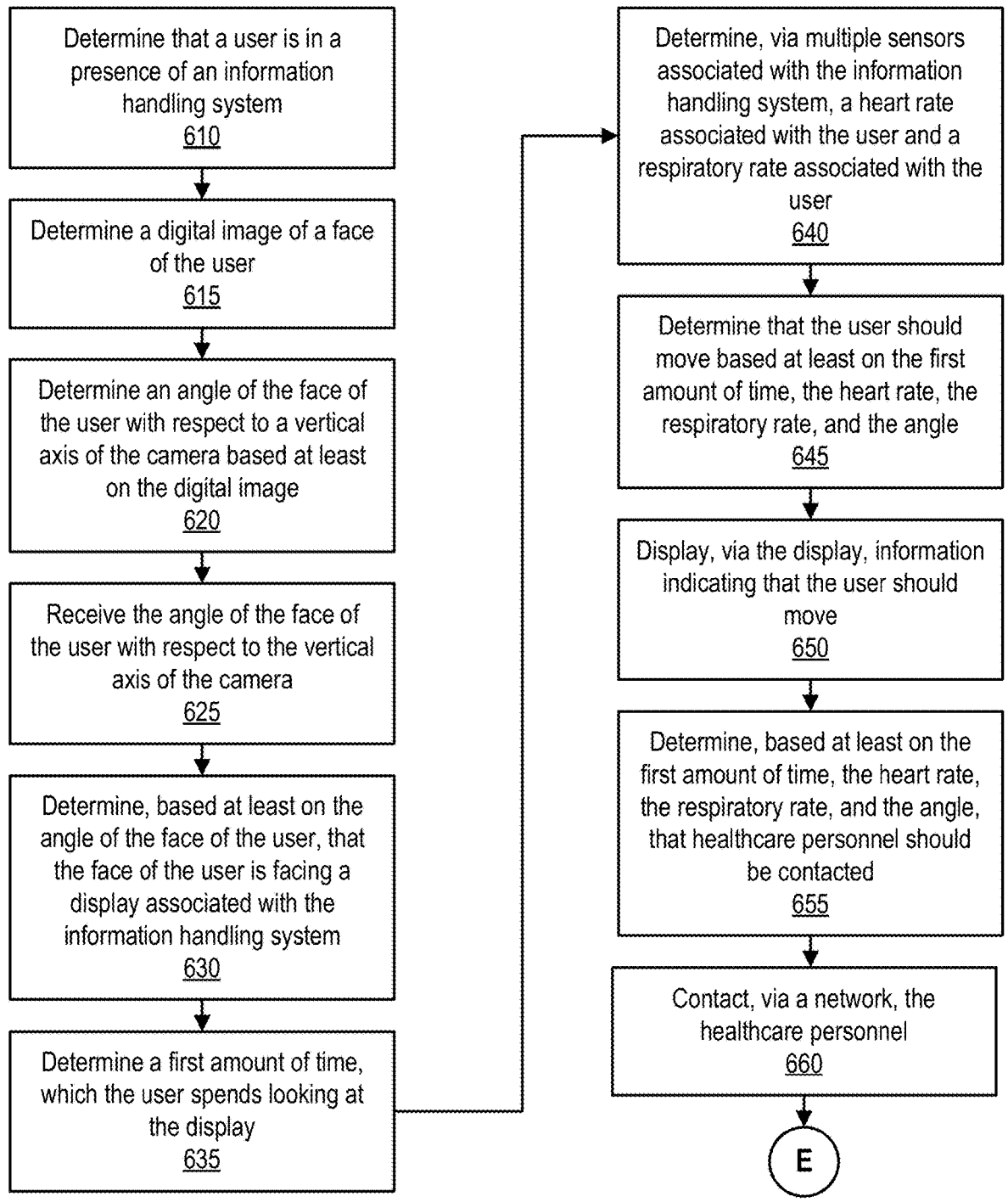
FIGS. 6A and 6B illustrate another example of a method of operating a digital wellbeing system is illustrated, according to one or more embodiments.
Figure 6B:
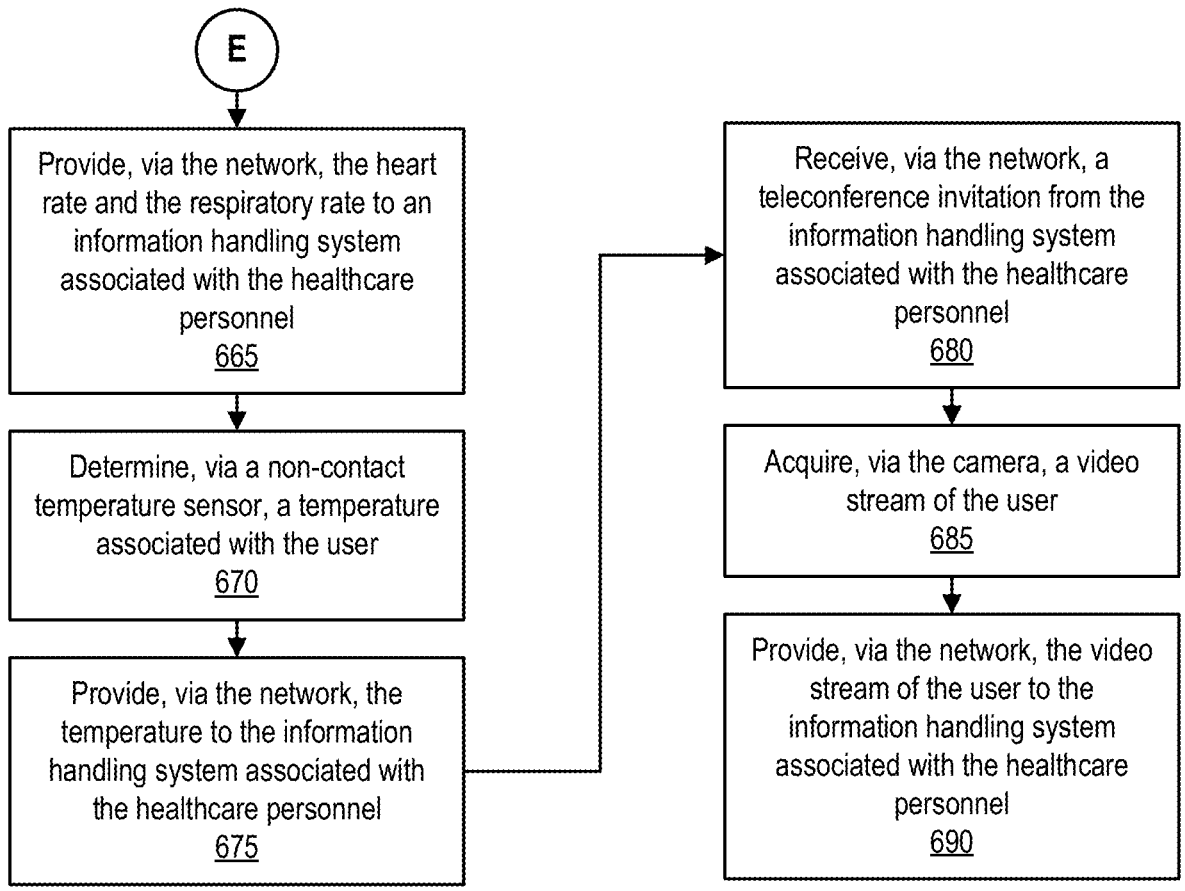

Turning now to FIGS. 6A and 6B, another example of a method of operating a digital wellbeing system is illustrated, according to one or more embodiments. At 610, it may be determined that a user is in a presence of the information handling system. In one example, it may be determined that user 190 is in a presence of IHS 110 via camera 184. For instance, it may be determined that user 190 is in a presence of IHS 110 via AON 538 of camera 184. In another example, it may be determined that user 190 is in a presence of IHS 110 via a ToF sensor associated with IHS 110. In one instance, the ToF sensor may be external to IHS 110. In another instance, IHS 110 may include the ToF sensor. In one or more embodiments, determining that a user is in a presence of the information handling system may include that the user is within a distance of the information handling system. For example, determining that a user is in a presence of the information handling system may include that the user is within two meters of the information handling system.

At 615, a digital image of a face of the user may be determined. For example, camera 184 may determine a digital image of a face of user 190. At 620, an angle of the face of the user with respect to a vertical axis of the camera may be determined based at least on the digital image. For example, camera 184 may determine an angle of the face of user 190 with respect to a vertical axis of camera 184 based at least on the digital image. In one or more embodiments, camera 184 may utilize and/or implement a convolution neural network to determine the angle of the face of user 190 with respect to the vertical axis of camera 184 based at least on the digital image. For example, the convolution neural network may receive the digital image as input.

At 625, the angle of the face of the user with respect to the vertical axis of the camera may be received. For example, microcontroller 130 may receive the angle of the face of user 190 with respect to the vertical axis of camera 184. At 630, it may be determined, based at least on the angle of the face of the user, that the face of the user is facing a display associated with the information handling system. For example, microcontroller 130 may determine, based at least on the angle of the face of user 190, that the face of user 190 is facing display 182 associated with IHS 110.

At 635, a first amount of time, which the user spends looking at the display may be determined. For example, microcontroller 130 may determine a first amount of time, which the user spends looking at the display. In one or more embodiments, the first amount of time, which the user spends looking at the display may be determined after determining that the face of the user is facing the display. At 640, a heart rate associated with the user and a respiratory rate associated with the user may be determined via multiple sensors associated with the information handling system. For example, microcontroller 130 may determine, via multiple of sensors 185, a heart rate associated with user 190 and a respiratory rate associated with user 190.

At 645, it may be determined that the user should move based at least on the first amount of time, the heart rate, the respiratory rate, and the angle. For example, microcontroller 130 may determine that user 190 should move based at least on the first amount of time, the heart rate, the respiratory rate, and the angle. At 650, information indicating that the user should move may be displayed via the display. For example, IHS 110 may display, via display 182, information indicating that user 190 should move. In one or more embodiments, rather than or in addition to indicating, via the display, information that the user should move, one or more sounds may be produced. For example, the sounds produced may indicate that the user should move. In one or more embodiments, rather than or in addition to indicating, via the display, information that the user should move, one or more haptic vibrations may be produced. For example, the haptic vibrations produced may indicate that the user should move.

At 655, it may be determined, based at least on the first amount of time, the heart rate, the respiratory rate, and the angle, that healthcare personnel should be contacted. For example, digital wellbeing service 515 may determine, based at least on the first amount of time, the heart rate, the respiratory rate, and the angle, that healthcare personnel should be contacted.

At 660, the healthcare personnel may be contacted via a network. For example, digital wellbeing service 515 may contact, via a network, the healthcare personnel. In one or more embodiments, a network may include a wired network, a wireless network, an optical network, or a combination of the foregoing, among others. For example, the network may include and/or be coupled to various types of communications networks. For instance, the network may include and/or be coupled to a LAN, a WAN (e.g., a private WAN, a corporate WAN, a public WAN, etc.), an Internet, a public switched telephone network (PSTN), a cellular telephone network, a satellite telephone network, or a combination of the foregoing, among others.

At 665, the heart rate and the respiratory rate may be provided, via the network, to an information handling system associated with the healthcare personnel. For example, digital wellbeing service 515 may provide, via the network, the heart rate and the respiratory rate to an IHS 110 associated with the healthcare personnel. In one or more embodiments, the healthcare personnel may include one or more of a doctor, a nurse, a nurse practitioner, a physician's assistant, and medical staff associated with a medical facility, among others.

At 670, a temperature associated with the user may be determine via a non-contact temperature sensor. For example, microcontroller 130 may determine, via a non-contact temperature sensor, a temperature associated with user 190. At 675, the temperature may be provided, via the network, to the information handling system associated with the healthcare personnel. For example, digital wellbeing service 515 may provide, via the network, the temperature to the IHS 110 associated with the healthcare personnel.

At 680, a teleconference invitation from the information handling system associated with the healthcare personnel may be received via the network. For example, digital wellbeing service 515 may receive, via the network, a teleconference invitation from the IHS 110 associated with the healthcare personnel. At 685, a video stream of the user may be acquired via the camera. For example, digital wellbeing service 515 may acquire, via camera 184, a video stream of user 190. At 690, the video stream of the user may be provided, via the network, to the information handling system associated with the healthcare personnel. For example, digital wellbeing service 515 may provide, via the network, the video stream of the user to the IHS 110 associated with the healthcare personnel.

In one or more embodiments, one or more of the method and/or process elements and/or one or more portions of a method and/or a process element may be performed in varying orders, may be repeated, or may be omitted. Furthermore, additional, supplementary, and/or duplicated method and/or process elements may be implemented, instantiated, and/or performed as desired, according to one or more embodiments. Moreover, one or more of system elements may be omitted and/or additional system elements may be added as desired, according to one or more embodiments.

In one or more embodiments, a memory medium may be and/or may include an article of manufacture. For example, the article of manufacture may include and/or may be a software product and/or a program product. For instance, the memory medium may be coded and/or encoded with processor-executable instructions in accordance with at least a portion of one or more flowcharts, at least a portion of one or more systems, at least a portion of one or more methods, and/or at least a portion of one or more processes described herein to produce the article of manufacture.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An information handling system, comprising:
    at least one processor;
    a microcontroller coupled to the at least one processor;
    a plurality sensors coupled to the microcontroller;
    a camera coupled to the at least one processor; and
    a memory medium, coupled to the at least one processor, that stores instructions executable by the at least one processor, which when executed by the at least one processor, cause the information handling system to:
        determine that a user is in a presence of the information handling system;
        determine that a low power vision camera is not available at the information handling system;
        in response to determining that the low power vision camera is not available, determine that a time-of-flight proximity sensor is not available;
        in response to determining that the time-of-flight proximity sensor is not available, utilize a standard camera associated with the information handling system;
    wherein the standard camera is configured to:
        determine a digital image of a face of the user; and
        determine an angle of the face of the user with respect to a vertical axis of the camera based at least on the digital image;
    wherein the microcontroller is configured to:
        receive the angle of the face of the user with respect to the vertical axis of the camera;
        determine, based at least on the angle of the face of the user, that the face of the user is facing a display associated with the information handling system;
        after determining that the face of the user is facing the display, determine a first amount of time, which the user spends looking at the display;
        determine, via the plurality sensors associated with the information handling system, a heart rate associated with the user and a respiratory rate associated with the user;
        determine that the user should move based at least on the first amount of time, the heart rate, the respiratory rate, and the angle; and
    wherein the instructions further cause the information handling system to:
        display, via the display, information indicating that the user should move.

2. The information handling system of claim 1, wherein the instructions further cause the information handling system to:
    determine, based at least on the first amount of time, the heart rate, the respiratory rate, and the angle, that healthcare personnel should be contacted; and
    in response to determining that the healthcare personnel should be contacted:
        contact, via a network, the healthcare personnel; and
        provide, via the network, the heart rate and the respiratory rate to an information handling system associated with the healthcare personnel.

3. The information handling system of claim 2,
    wherein the microcontroller is further configured to determine, via a non-contact temperature sensor, a temperature associated with the user; and
    wherein the instructions further cause the information handling system to provide, via the network, the temperature to the information handling system associated with the healthcare personnel.

4. The information handling system of claim 2, wherein the instructions further cause the information handling system to:
    receive, via the network, a teleconference invitation from the information handling system associated with the healthcare personnel;
    acquire, via the standard camera, a video stream of the user; and
    provide, via the network, the video stream of the user to the information handling system associated with the healthcare personnel.

5. The information handling system of claim 1, wherein the microcontroller is further configured to determine a second amount of time, which the user not facing the display.

6. The information handling system of claim 1,
wherein the plurality of sensors include a radar device; and
wherein, to determine the heart rate associated with the user and respiratory rate associated with the user, the radar device is configured to determine at least one of the heart rate associated with the user and respiratory rate associated with the user.

7. A method, comprising:
determining that a user is in a presence of an information handling system;
determine that a low power vision camera is not available at the information handling system;
in response to determining that the low power vision camera is not available, determining that a time-of-flight proximity sensor is not available;
in response to determining that the time-of-flight proximity sensor is not available, utilizing a standard camera;
determining, by the standard camera associated with the information handling system, a digital image of a face of the user;
determining, by the standard camera, an angle of the face of the user with respect to a vertical axis of the camera based at least on the digital image;
receiving, by a microcontroller, the angle of the face of the user with respect to the vertical axis of the camera;
determining, based at least on the angle of the face of the user, that the face of the user is facing a display associated with the information handling system;
after the determining that the face of the user is facing the display, determining a first amount of time, which the user spends looking at the display;
determining, via a plurality sensors associated with the information handling system, a heart rate associated with the user and a respiratory rate associated with the user;
determining that the user should move based at least on the first amount of time, the heart rate, the respiratory rate, and the angle; and
displaying, via the display, information indicating that the user should move.

8. The method of claim 7, further comprising:
determining, based at least on the first amount of time, the heart rate, the respiratory rate, and the angle, that healthcare personnel should be contacted; and
in response to the determining that the healthcare personnel should be contacted:
contacting the healthcare personnel; and
providing, via a network, the heart rate and the respiratory rate to an information handling system associated with the healthcare personnel.

9. The method of claim 8, further comprising:
determining, via a non-contact temperature sensor, a temperature associated with the user; and
providing, via the network, the temperature to the information handling system associated with the healthcare personnel.

10. The method of claim 8, further comprising:
receiving, via the network, a teleconference invitation from the information handling system associated with the healthcare personnel;
acquiring, via the standard camera, a video stream of the user; and
providing, via the network, the video stream of the user to the information handling system associated with the healthcare personnel.

11. The method of claim 7, further comprising:
determining a second amount of time, which the user not facing the display.

12. The method of claim 7,
wherein the camera includes an always on (AON) system that implements a convolution neural network; and
wherein the determining, by the camera, the angle of the face of the user with respect to the vertical axis of the camera based at least on the digital image includes determining, by the convolution neural network, the angle of the face of the user with respect to the vertical axis of the camera based at least on the digital image.

13. The method of claim 7,
wherein the plurality of sensors include a radar device; and
wherein the determining the heart rate associated with the user and respiratory rate associated with the user includes determining, by the radar device, at least one of the heart rate associated with the user and respiratory rate associated with the user.

14. A digital wellbeing system, comprising:
an information handling system that includes at least one processor, a microcontroller coupled to the at least one processor, and a memory medium coupled to the at least one processor, which stores instructions executable by the at least one processor;
a display communicatively coupled to the at least one processor of the information handling system;
a standard camera communicatively coupled to the at least one processor of the information handling system; and
a plurality of sensors communicatively coupled to the microcontroller;
wherein the microcontroller is configured to:
determine, based on the plurality of sensors, that a user is in a presence of the information handling system;
determine that a low power vision camera is not available at the information handling system;
in response to determining that the low power vision camera is not available, determine that a time-of-flight proximity sensor is not available;
in response to determining that the time-of-flight proximity sensor is not available, utilize a standard camera associated with the information handling system;
wherein the standard camera is configured to:
determine a digital image of a face of the user; and
determine an angle of the face of the user with respect to a vertical axis of the camera based at least on the digital image;
wherein the microcontroller is further configured to:
receive the angle of the face of the user with respect to the vertical axis of the camera;
determine, based at least on the angle of the face of the user, that the face of the user is facing a display associated with the information handling system;
after determining that the face of the user is facing the display, determine a first amount of time, which the user spends looking at the display;
determine, via the plurality sensors associated with the information handling system, a heart rate associated with the user and a respiratory rate associated with the user; and
determine that the user should move based at least on the first amount of time, the heart rate, the respiratory rate, and the angle; and
wherein the instructions cause the information handling system to:

display, via the display, information indicating that the user should move.

15. The digital wellbeing system of claim 14, wherein the instructions further cause the information handling system to:
    determine, based at least on the first amount of time, the heart rate, the respiratory rate, and the angle, that healthcare personnel should be contacted; and
    in response to determining that the healthcare personnel should be contacted:
    contact, via a network, the healthcare personnel; and
    provide, via the network, the heart rate and the respiratory rate to an information handling system associated with the healthcare personnel.

16. The digital wellbeing system of claim 15,
    wherein the microcontroller is further configured to determine, via a non-contact temperature sensor, a temperature associated with the user; and
    wherein the instructions further cause the information handling system to provide, via the network, the temperature to the information handling system associated with the healthcare personnel.

17. The digital wellbeing system of claim 15, wherein the instructions further cause the information handling system to:
    receive, via the network, a teleconference invitation from the information handling system associated with the healthcare personnel;
    acquire, via the standard camera, a video stream of the user; and
    provide, via the network, the video stream of the user to the information handling system associated with the healthcare personnel.

18. The digital wellbeing system of claim 14,
    wherein the camera includes an always on (AON) system that implements a convolution neural network; and
    wherein, to determine the angle of the face of the user with respect to the vertical axis of the camera based at least on the digital image, the convolution neural network is configured to determine the angle of the face of the user with respect to the vertical axis of the camera based at least on the digital image.

19. The digital wellbeing system of claim 14,
    wherein the plurality of sensors include a radar device; and
    wherein, to determine the heart rate associated with the user and respiratory rate associated with the user, the radar device is configured to determine at least one of the heart rate associated with the user and respiratory rate associated with the user.

* * * * *